US010548657B2

(12) United States Patent
Goode et al.

(10) Patent No.: US 10,548,657 B2
(45) Date of Patent: Feb. 4, 2020

(54) SYSTEMS AND METHODS SYSTEMS RELATED TO ELECTROSURGICAL WANDS WITH SCREEN ELECTRODES

(71) Applicant: ArthroCare Corporation, Austin, TX (US)

(72) Inventors: Johnson E. Goode, Austin, TX (US); Mark Bieberich, Lakeway, TX (US); Philip M. Tetzlaff, Austin, TX (US); Jean Woloszko, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 380 days.

(21) Appl. No.: 15/383,814

(22) Filed: Dec. 19, 2016

(65) Prior Publication Data

US 2017/0095285 A1    Apr. 6, 2017

Related U.S. Application Data

(63) Continuation of application No. 14/192,978, filed on Feb. 28, 2014, now Pat. No. 9,526,556.

(51) Int. Cl.
*A61B 18/04* (2006.01)
*A61B 18/14* (2006.01)
(Continued)

(52) U.S. Cl.
CPC ........... *A61B 18/14* (2013.01); *A61B 18/042* (2013.01); *A61B 18/148* (2013.01);
(Continued)

(58) Field of Classification Search
CPC ............ A61B 18/00577; A61B 18/148; A61B 18/042; A61B 2018/00577;
(Continued)

(56) References Cited

U.S. PATENT DOCUMENTS 6,254,600 B1     7/2001  Willink et al.
9,526,556 B2 *  12/2016  Goode ................. A61B 18/042
(Continued)

FOREIGN PATENT DOCUMENTS

GB    2451623     2/2009
WO    03068311    8/2003

OTHER PUBLICATIONS

AU Office Action for AU App No. 2014384594 dated Dec. 5, 2018, 5 pages.
(Continued)

*Primary Examiner* — Linda C Dvorak
*Assistant Examiner* — Annabeth E Rodriguez
(74) *Attorney, Agent, or Firm* — Norman F. Hainer, Jr.

(57) ABSTRACT

An electrosurgical wand for treating tissue at a target site within or on a patient's body is described, having an elongate shaft with a handle and a distal end portion. The distal end portion has an active electrode, an insulative spacer body and a return electrode; the active electrode supported by the insulative spacer body and spaced away from the return electrode. The active electrode has both lateral and medial edge surfaces. The insulative spacer body has an aspiration cavity fluidly connected with an aspiration lumen, and at least one tapered aperture extending beyond at least one of the electrode medial edge surfaces and directed to the aspiration cavity.

19 Claims, 7 Drawing Sheets

(51) Int. Cl.
 *A61B 18/16* (2006.01)
 *A61B 18/00* (2006.01)

(52) U.S. Cl.
 CPC ........... *A61B 2018/00577* (2013.01); *A61B 2018/1405* (2013.01); *A61B 2018/162* (2013.01); *A61B 2218/007* (2013.01)

(58) Field of Classification Search
 CPC ...... A61B 2018/1405; A61B 2018/162; A61B 2018/007; A61B 2218/1514; A61B 2218/001; A61B 2218/007; A61B 10/0283; A61B 2010/045; A61B 18/14; A51B 5/0183; A61M 1/0039; A61M 1/0058; A61C 17/0043

See application file for complete search history.

(56) References Cited

U.S. PATENT DOCUMENTS

| | | | |
|---|---|---|---|
| 2003/0097129 A1 | 5/2003 | Davison et al. | |
| 2003/0225403 A1* | 12/2003 | Woloszko | A61B 18/148 606/41 |
| 2009/0048592 A1* | 2/2009 | Thomas | A61B 18/148 606/33 |
| 2010/0204690 A1 | 8/2010 | Bigley et al. | |
| 2013/0331836 A1* | 12/2013 | Keogh | A61B 18/1482 606/41 |
| 2014/0200581 A1* | 7/2014 | Aluru | A61B 18/14 606/48 |

OTHER PUBLICATIONS

CN Office Action for CN Application No. 201480078582.3 dated Dec. 31, 2014, 19 pages.

* cited by examiner

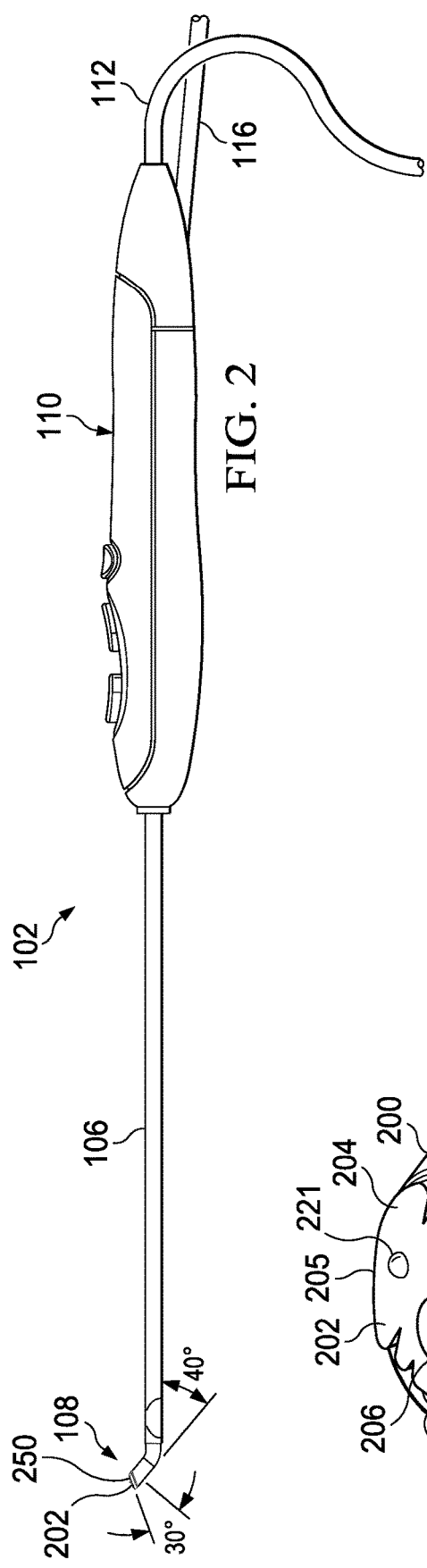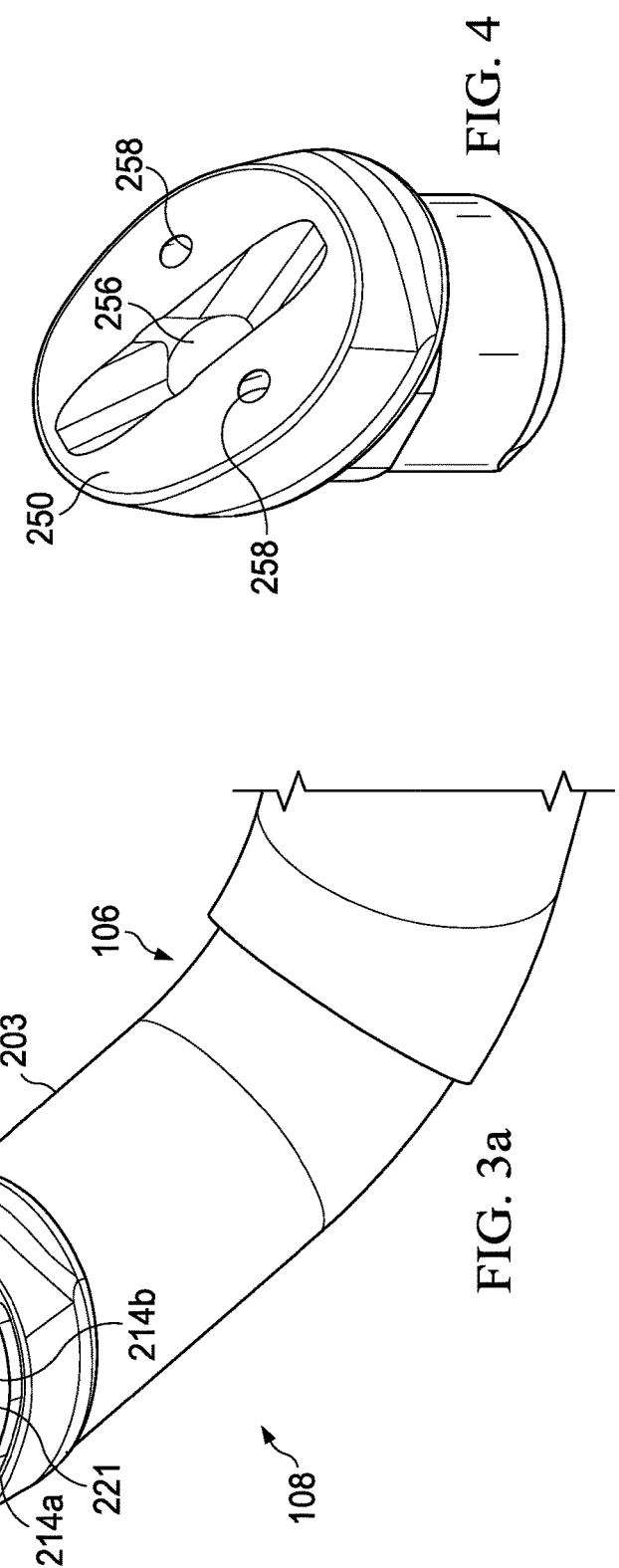

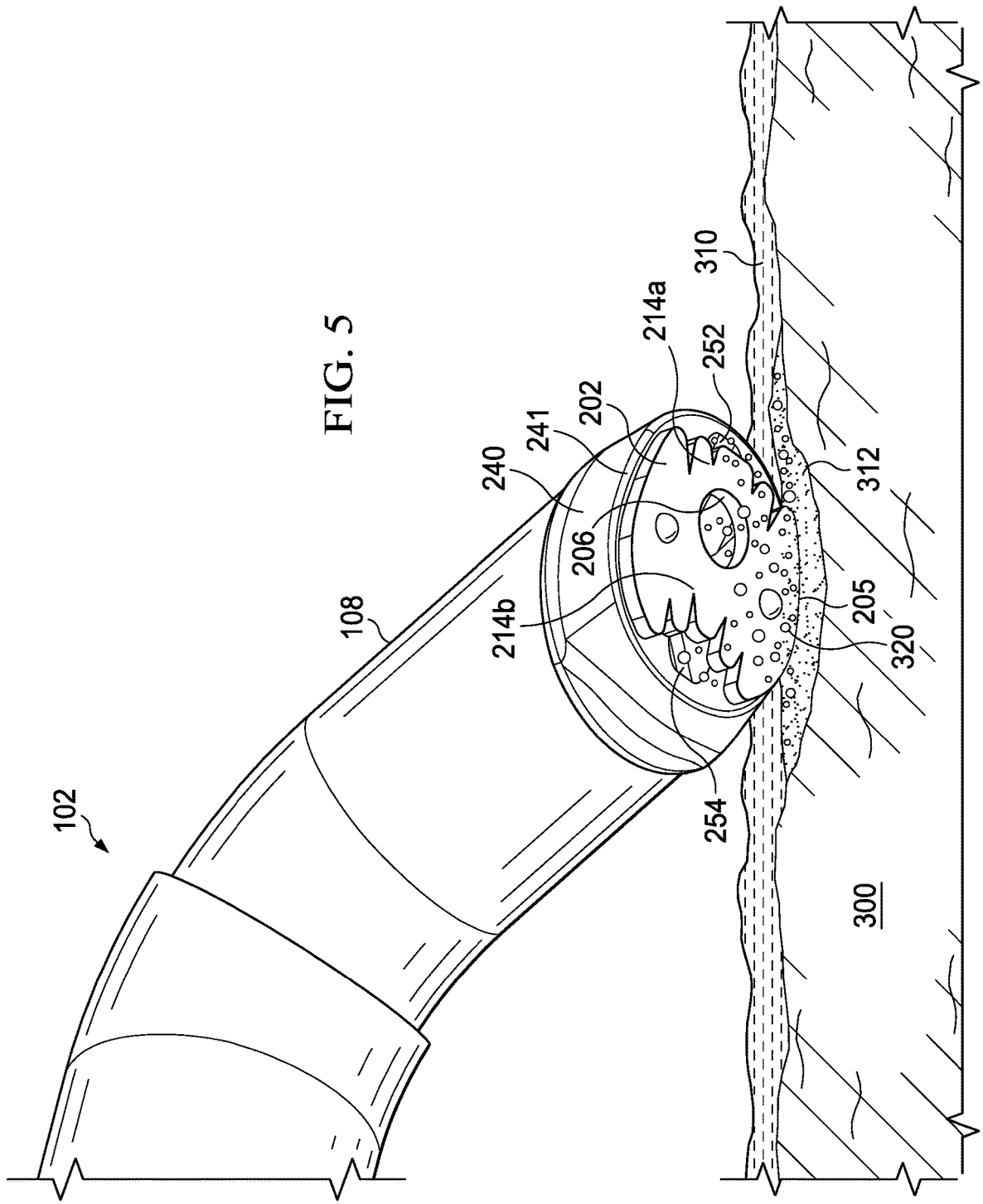

SYSTEMS AND METHODS SYSTEMS RELATED TO ELECTROSURGICAL WANDS WITH SCREEN ELECTRODES

CROSS-REFERENCE TO RELATED APPLICATIONS

This application is a continuation of U.S. patent application Ser. No. 14/192,978 filed Feb. 28, 2014, the complete disclosure of which is incorporated herein by reference for all purposes.

FIELD OF THE INVENTION

The present invention relates generally to the field of electrosurgery, and more particularly to apparatus and methods for applying high frequency voltage to ablate tissue. More particularly, the present invention relates to apparatus and methods for securing a substantially flat screen-type active electrode to the distal tip of the shaft of an electrosurgical instrument and methods of fluid aspiration.

BACKGROUND

Electrosurgical systems are used by physicians to perform specific functions during surgical procedures. For example, in an ablation mode electrosurgical systems use high frequency electrical energy to remove soft tissue such as sinus tissue, adipose tissue or other tissue such as meniscus, or cartilage or synovial tissue in a joint.

Conventional electrosurgical methods are widely used because they generally achieve hemostasis and reduce patient bleeding associated with tissue cutting operations while improving the surgeon's visibility of the treatment area. Many of the electrosurgical devices used in electrosurgery include a method of removing fluid, debris and bubbles from the field, so as to improve the clinician's visibility around the target tissue area. However, in the case of some electrosurgical devices where sufficient fluid is required to achieve certain clinical effects, such as ablation, fluid removal needs to be balanced or targeted in optimal locations. This may allow sufficient fluid for vapor layer or plasma generation while minimizing debris and bubbles in the field. Many devices also make use of a screen-type active electrode which is typically cut, or etched, from a sheet of conductive material. These electrosurgical devices and procedures, however, may suffer from a number of disadvantages. For example, screen-type active electrodes typically require some method of securement to an insulative body and furthermore to the distal tip of the device itself. Failure to adequately secure the screen electrode to the insulative body may result in improper device function.

Prior attempts to secure the screen active electrode to the insulative body have involved mechanical, thermal, and chemical means or various combinations thereof. Numerous mechanical forms of securement have been utilized, while adhesives have been used as a chemical form of joining, and welding the screen may provide a thermal method of joining. These mechanical joining methods may also include the use of plastic, or non-recoverable, deformations of the materials being used for securement. However, even in combination with other joining methods, all methods for fixation provide solutions that typically are challenged over extended periods of use, due to thermal degradation and plasma degradation. Optimum positioning of the screen electrode fixation with these methods of degradation therefore must be incorporated.

Accordingly, devices and methods which allow targeted fluid aspiration relative to ablation surfaces or edges are desired. Additionally, devices for the securement of flat screen active electrodes to the insulative body of an electrosurgical instrument while maintaining electrical connections through the insulative body are desired. In particular, mechanical methods for providing durable securement of an electrically connected screen active electrode to the insulative body at the distal tip of an electrosurgical device, while providing enhanced electrosurgical operating parameters are desired.

SUMMARY OF THE INVENTION

The present invention provides systems, apparatus and methods for aspirating fluid, debris and gas bubbles from the surgical field and the surgeon's field of view with minimal interruption to the vapor layer. The present disclosure also provides systems, apparatus and methods for mechanically securing a screen type active electrode to the insulative body at the distal tip of an electrosurgical device. Further the present disclosure provides systems and apparatus for creating high current density with internal pointed geometries to decelerate wear on a screen electrode.

In one aspect of the invention, the present disclosure describes an electrosurgical wand for treating tissue using a high frequency voltage delivered to a target site within or on a patient's body. The wand includes an elongate shaft with a handle end and a distal end portion, the distal end portion having an electrode assembly and an insulative spacer body. The electrode assembly includes both a substantially flat active screen electrode and a return electrode spaced from the active screen electrode. The return electrode may be spaced proximally from the active screen electrode and may be part of the elongate shaft. The active electrode is intended to contact tissue and has a relatively large tissue contacting surface and a perimeter or edge surface. The insulative spacer body contacts tissue in places, and also serves to support and electrically insulate the active screen electrode. An aspiration cavity is disposed within the spacer body with an elongate opening at the tissue contacting surface partially covered by the active screen electrode, while a portion of the elongate cavity opening extends beyond a portion of the screen electrode edge surface. The tissue contacting surface includes a first aspiration aperture having a first aperture perimeter, a portion of the first aperture perimeter being defined by part of the edge surface of the screen electrode and also part of the aspiration cavity.

Another configuration of the electrosurgical device according to the present disclosure is an electrosurgical wand for treating tissue at a surgical site with an elongate housing, defining a handle end and a tissue contacting surface at a distal end. Part of the tissue contacting surface includes an active screen electrode which is disposed on an insulative spacer, this spacer also making up part of the tissue contacting surface. The active screen electrode includes at least one lateral edge surface, free of any asperities such as surface geometry or texture that may create an area of high current density such as pointed features or roughened surface, and medial surfaces such as distal and proximal edge surfaces that have at least one asperity such as one pointed geometry feature or area of higher current density. The tissue contacting surface also includes a first aspiration aperture spaced at a discrete location away from the at least one lateral edge surface so as to not disrupt any plasma or vapor layer proximate the lateral edge surface. This aperture is in fluid communication with an aspiration lumen disposed within the wand and may remove any debris or gas bubbles from the surgical site. This first aperture has a perimeter that includes a portion of an insulating spacer cavity and a portion of either the electrode distal edge surface or the electrode proximal edge surface.

In another aspect of the disclosure, a method of treating a target tissue using an electrosurgical wand is described, the method including placing a distal end portion of the wand near a target tissue, the distal end portion including a substantially flat active screen electrode being supported by an insulative spacer. A high frequency voltage may then be applied between the active electrode and a return electrode that is spaced away from the active electrode, the high frequency voltage is sufficient to generate a vapor layer near a tissue contacting surface of the active electrode. The distal end portion may then be oriented so that a lateral edge surface of the active electrode is near the target tissue so as to use this edge surface, primarily to treat the target tissue. Tissue fragments and gas bubbles may then be aspirated away through at least one aspiration aperture that is located in a discrete area that is spaced away from the lateral edge surface. This is so as to not disrupt the vapor layer proximate the active electrode lateral edge surface, to therefore maintain a uniform vapor layer near the lateral edge surface so as to create a more consistent electrosurgical tissue effect. The at least one aspiration aperture has a portion of its perimeter made up by the active screen electrode and a portion by a spacer aspiration cavity.

BRIEF DESCRIPTION OF THE DRAWINGS

For a detailed description of exemplary embodiments, reference will now be made to the accompanying drawings in which:

FIG. 2 shows an electrosurgical wand in accordance with at least some embodiments;

FIG. 3a shows a perspective view of a wand distal end in accordance with at least some embodiments;

FIG. 4 shows a perspective view of an insulating spacer of a wand in accordance with at least some embodiments;

FIG. 5 shows an elevation view of the distal end of a wand treating tissue in accordance with at least some embodiments;

NOTATION AND NOMENCLATURE

Figure 1:
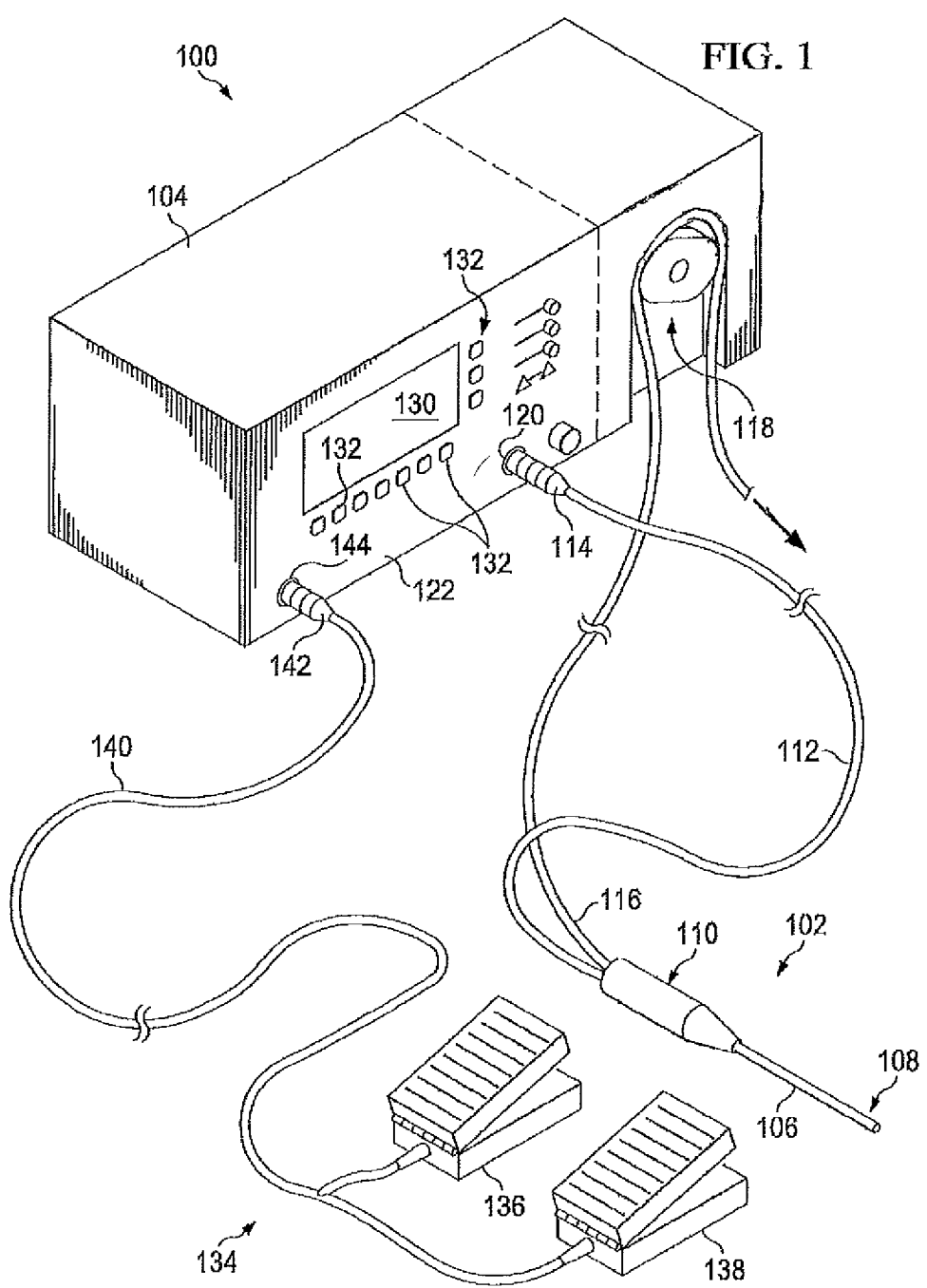
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment, and/or an electrode having a voltage induced thereon by a voltage generator.

"Return electrode" shall mean an electrode of an electrosurgical wand which serves to provide a current flow path for electrons with respect to an active electrode, and/or an electrode of an electrosurgical wand which does not itself produce an electrically-induced tissue-altering effect on tissue targeted for treatment.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

The present invention provides systems and methods for selectively applying electrical energy to a target location within or on a patient's body. The present invention is particularly useful in procedures where the tissue site is flooded or submerged with an electrically conducting fluid, such as arthroscopic surgery of the knee, shoulder, ankle, hip, elbow, hand or foot. In other procedures, the present invention may be useful for collagen shrinkage, ablation and/or hemostasis in procedures for treating target tissue alone or in combination with the volumetric removal of tissue. More specifically, the embodiments described herein provide for electrosurgical devices characterized by a substantially flat and relatively thin screen active electrode disposed at the distal tip of the device. Additionally, the present embodiments include apparatus and methods for the targeted aspiration of fluid and debris away from the surgical field as well as methods of mechanical securement of the screen electrode and wear resistant design features to the screen electrode. These embodiments may extend the operating period of the electrosurgical device by providing a more wear resistant electrode to plasma and a more robust electrode securement method of attachment. These embodiments may also improve the surgeon's visibility of the surgical field while minimizing any disruption to a vapor layer around the screen electrode and hence any disruption to the intended tissue effect.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

FIG. 1 illustrates an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104"). The wand 102 comprises an elongate housing or elongate shaft 106 that defines distal end 108. The elongate shaft 106 further defines a handle or proximal end 110, where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116, used to provide aspiration at the distal end portion 108 of the wand. In accordance with various embodiments, the tubular member 116 couples to a peristaltic pump 118, the pump being illustratively shown as an integral component with the controller 104. In other embodiments, an enclosure for the peristaltic pump 118 may be separate from the enclosure 122 for the controller 104 (as shown by dashed lines in the figure), but in any event the peristaltic pump is operatively coupled to the controller 104. In the context of the various embodiments, the peristaltic pump 118 creates a volume-controlled aspiration from a surgical field at the distal end portion 108 of the wand 102.

Still referring to FIG. 1, a display device or interface device 130 is visible through the enclosure 122 of the controller 104, and in some embodiments a user may select operational modes of the controller 104 by way of the interface device 130 and related buttons 132. In some embodiments the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller 104 may comprise a corresponding connector 144 that couples to the pedal connector 142. A physician may use the foot pedal assembly 134 to control various aspects of the controller 104, such as the operational mode. For example, pedal device 136 may be used for on-off control of the application of radio frequency (RF) energy to the wand 102. Further, pedal device 138 may be used to control and/or set the mode of ablation of the electrosurgical system. In certain embodiments, control of the various operational or performance aspects of controller 104 may be activated by selectively depressing finger buttons located on handle 110 of wand 102 (the finger buttons not specifically shown so as not to unduly complicate the figure).

The electrosurgical system 100 of the various embodiments may have a variety of operational modes. One such mode employs Coblation® technology. In particular, the assignee of the present disclosure is the owner of Coblation® technology. Coblation® technology involves the application of RF energy between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline. In some embodiments the electrically conductive fluid is delivered in the vicinity of the active electrodes and/or to the target site by the wand 102.

When the electrically conductive fluid is heated to the point that the atoms of the fluid vaporize faster than the atoms condense, a vapor or gas is formed. When sufficient energy is applied to the vapor or gas, the atoms collide with each other causing a release of electrons in the process, and an ionized gas, ionized vapor layer, or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

In addition to the Coblation® mode, the electrosurgical system 100 of FIG. 1 is also useful for sealing larger arterial vessels (e.g., on the order of about 1 millimeter (mm) in diameter), when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 may also have a coagulation mode where RF energy at a second, lower voltage is applied to one or more active electrodes (either the same or different electrode(s) as the ablation mode) sufficient to heat, shrink, seal, fuse, and/or achieve homeostasis of severed vessels within the tissue.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons.

FIG. 2 illustrates a view of the wand 102 in accordance with example systems. In the illustrated embodiment the elongate shaft 106 is made of a metallic material (e.g., Grade TP304 stainless steel hypodermic tubing), and in some cases the elongate shaft 106 also defines a return electrode for the system. The wand 102 such as the embodiment shown in FIG. 2 may be designed for surgical procedures involving the knee or hip. The illustrated embodiment's elongate shaft 106 has a circular cross-sectional shape with a bend towards the distal end 108, orienting distal end 108 approximately 40° relative to the elongate axis of the proximal portion of shaft 106. Additionally distal end surface is oriented at an angle to the elongate axis of the shaft 106, cut at approximately a 30° angle relative to the distal end of the shaft 106, to define an oval shaped distal end surface 250 (better illustrated in FIGS. 3a and 3b). This provides for a lower wand distal end profile in order to accommodate space restrictions and posterior anatomy access. For embodiments where the cross-sectional shape of the elongate shaft 106 is circular, the outside diameter may be on the order of about 3 millimeters (mm), but larger and smaller dimensions may be used.

Figure 3B:
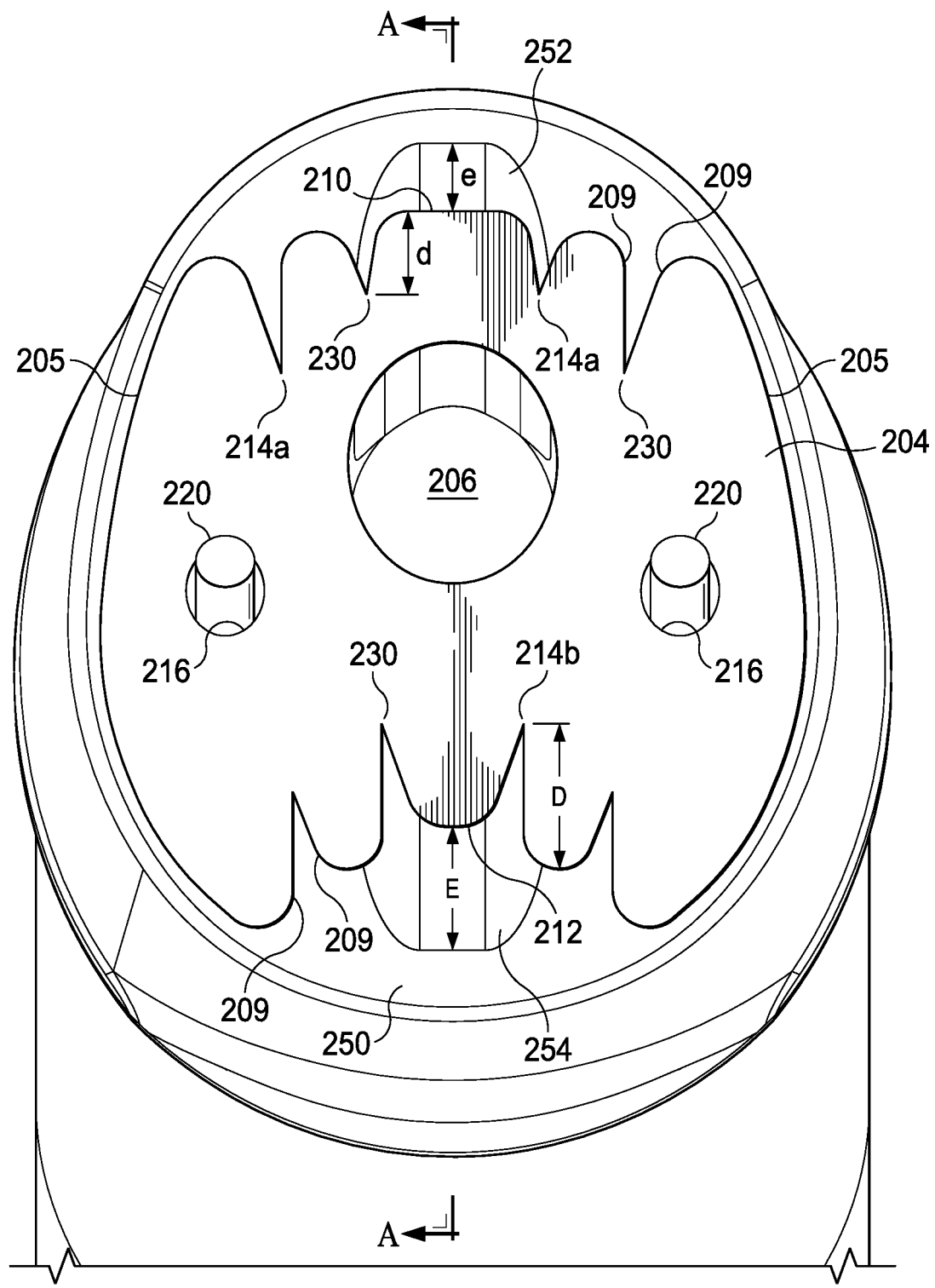
FIG. 3b illustrates a view of a wand contact surface in accordance with at least some embodiments.
Figure 3C:
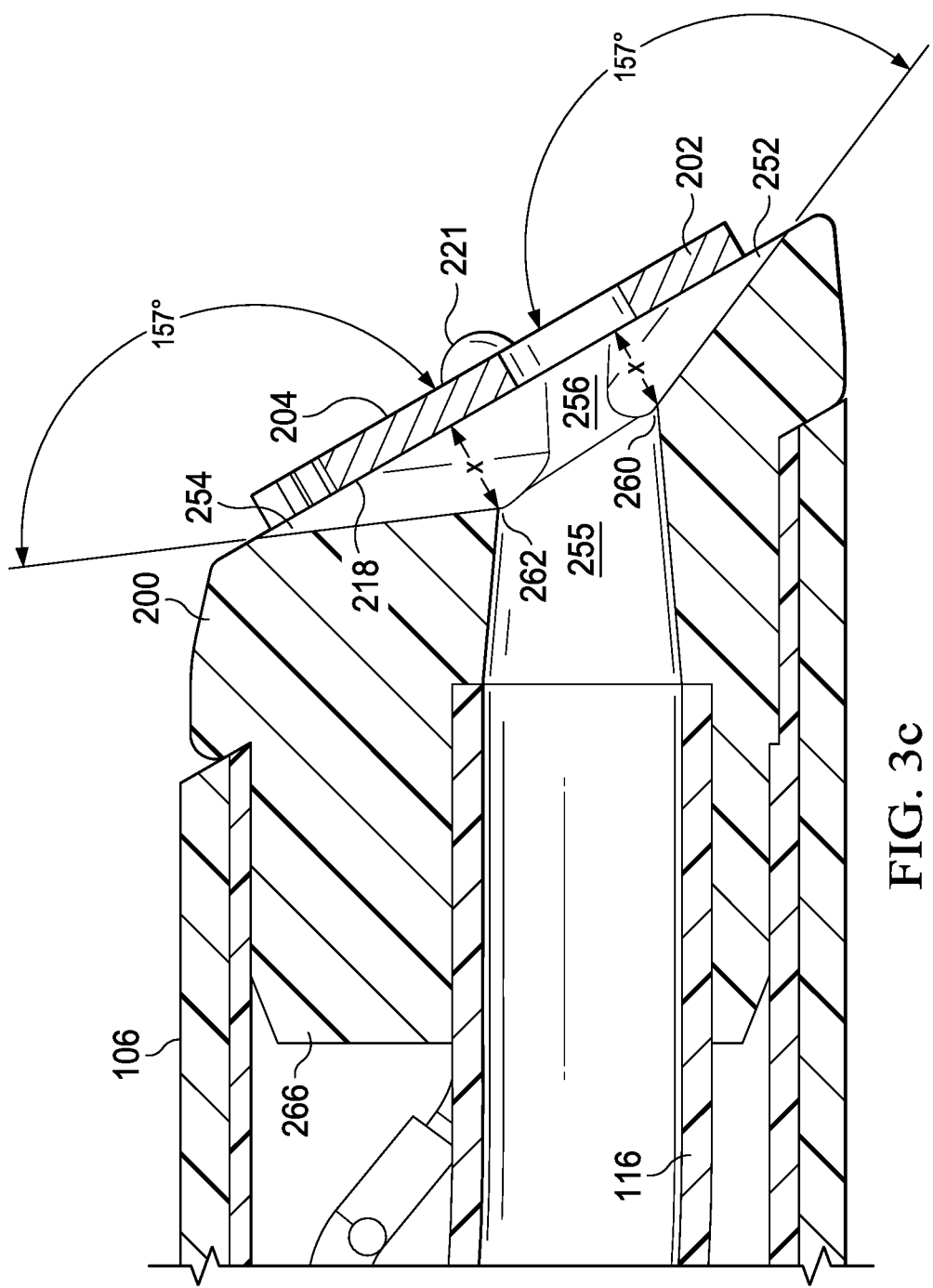
FIG. 3c shows a wand distal end cross-sectional view in accordance with at least some embodiments.

In embodiments where the elongate shaft is metallic, the distal end portion 108, as illustrated in FIG. 3a, may further comprise an electrically insulative spacer 200 coupled to the elongate shaft 106. In some cases spacer 200 is ceramic, but other non-conductive materials resistant to degradation when exposed to plasma may be equivalently used (e.g., glass). Spacer 200 may couple to the elongate shaft 106 in any suitable manner, such as telescoping within an inside diameter of the elongate shaft 106, by telescoping over the elongate shaft 106, and/or by use of adhesive. As shown in FIG. 3c, spacer 200 has a telescoping portion 266 operable to be placed within the internal diameter of the elongate housing 106 and in some cases the spacer may be at least partially held in place by an adhesive. Spacer 200 supports at least one active screen electrode 202 constructed of metallic or electrically conductive material. Spacer 200 thus electrically insulates active electrode 202 from the elongate shaft 106, as the elongate shaft 106 may act as the return electrode 203. In some embodiments, only a portion of elongate shaft 106 is exposed to act as return electrode 203, with the remaining portion of shaft 106 covered with an insulating material.

The illustrative active screen electrode 202 may comprise a conductive material, such as tungsten, titanium, molybdenum, stainless steel, aluminum, gold, copper or the like. Screen electrode 202 may have a diameter in the range of about 0.5 to 8 mm, preferably about 1 to 4 mm, and a thickness of about 0.05 to about 2.5 mm, preferably about 0.1 to 0.5 mm. Screen electrode 202 may have a variety of different shapes, such as the shape shown in FIGS. 3a and 3b, including at least one lateral edge surface 205 having a continuous edge surface free of any asperities such as pointed geometries. Lateral edge surface 205 is laterally spaced away from all aspiration apertures, such as aperture 206, 254 and 252 that are disposed more medially on the wand 102, so that a vapor layer may form adjacent a lateral edge surface 205 and remain relatively undisturbed during any aspiration. Screen electrode 202 may also include medial edge surfaces, such as a distal edge surface 210 and proximal edge surface 212, at least one of which may include at least one asperity such as an internal pointed geometry feature or cusp 214a, b, or some form of pointed or edged surface geometry. A surface asperity such as an internal pointed geometry feature creates a point of higher current density that leads to a preferential point of vapor layer initiation and potentially plasma generation on the active electrode 202. Without cusps 214a, b, vapor layer initiation may require higher voltages. Illustrated best in FIGS. 3a and 3b, active electrode 202 has four inverted cusps 214a of varying sizes disposed on the distal edge surface 210 and another four inverted cusps 214b of varying sized on the proximal edge surface 212. These are disposed at a specific, distinct location advantageous for enhanced vapor layer formation and potentially subsequent plasma formation, but spaced medially away from lateral edge surfaces 205.

In particular, inverted cusps 214a, b may be defined by curved portions 209 that tangentially intersect at a point 230. Inverted cusps 214a, b have a consistent or uniform shape throughout the thickness of active electrode 202, so that the point of intersection 230 creates an elongated surface or line, with minimal transition or radius between adjacent curved portions 209, through the thickness of screen electrode 202. Inverted cusps 214a, b create a point of vapor layer initiation to improve vapor layer formation and potentially plasma formation, proximate the point of intersection 230 for smooth tissue cutting. Unlike other plasma and vapor layer initiating asperities known in the art, such as externally protruding points or alternatively edges or corners of electrodes, the inverted cusp provides a vapor layer initiation point that minimizes tissue snagging during wand and electrode motion across tissue surfaces during tissue treatment. Additionally, the use of inverted cusps 214a, b as formed by intersection 230 appear to provide the unexpected benefit of more consistent and predicable patterns of active electrode 202 material wear and erosion. Illustrated best in FIG. 3b, inverted cusps 214a and 214b have a variety of depths and curves so that point 230 may be spaced to varying degrees from the electrode distal edge surface 210 or the proximal edge surface 212. It has been found during typical wand operation that the distal edge surface 210 tends to preferentially erode relative to the proximal edge surface 212. One reason for this is as a result of a typical wand orientation during tissue treatment, which leads to a preferred vapor layer initiation at the more distal portion of the electrode 202. The inventors have also found that in this particular orientation the flow rate of fluid drawn into the aspiration aperture is higher at the distal portion of electrode 202 and as drawn into aperture 252. Erosion rates of the material of electrode 202 have been found to be directly related to the proximity of the cusps to areas of higher fluid aspiration. Therefore, adjacent to aspiration apertures with relatively higher rates of fluid flow (e.g., adjacent aperture 252 in the presently describe configuration), distal cusps 214a have a first or reduced depth (d) relative to cusps 214b with a second depth D, or larger depth D to accommodate these differing erosion rates. By adjusting the depth of the cusps in areas with proximity to preferred vapor layer initiation characteristics and higher fluid aspiration rates, the inventors have found that the useful life of electrode 202 may be extended.

Screen electrode 202 may comprise aspiration aperture 206 having sizes and configurations that may vary depending on the particular application. Electrode aspiration aperture 206 will typically be large enough to allow ablated tissue fragments to pass through into an aspiration cavity and suction lumen (described in later figures) within insulative spacer 200 and flexible tubular member 116. Electrode aspiration aperture 206 is disposed in approximately the centre of the active electrode 202 and is spaced away from at least one lateral edge surface 205. Shown here, aspiration aperture 206 is spaced approximately equidistant between the two lateral edge surfaces 205. Screen electrode 202 may also have at least one securing wire aperture 216 sized to receive a securing wire or ribbon 220 operable to secure active screen electrode 202 to spacer 200. Wire or ribbon 220 may comprise a conductive material, such as platinum iridium and is operable to perform multiple functions. Firstly securement wire 220 is electrically connected with cable 112, disposed within elongate shaft 106 as well as active screen electrode 202, so as to be part of the electrical conduit through which the RF controller 104 delivers energy to the active screen electrode 202. Securement ribbon 220 may protrude through the at least one securing wire aperture 216 (as shown in FIG. 3b) and be processed so as to provide both a permanent electrical contact and mechanical securement with the active electrode 202 (shown in welded form 221 in FIG. 3a). This process may include laser spot welding. Securement wire 220 is preferably constructed from a material having a lower melting temperature than the active screen electrode material so as to melt readily during laser spot welding without affecting the grain structure of the active electrode 202. Structural changes to the active electrode 202 may reduce resistance to plasma degradation during the use. Securement wire 220 must also comprise a material with substantial resistance to plasma degradation itself, so that the laser spot weld, and hence mechanical securement and electrical continuity, minimally degrades with use.

Screen electrode 202 has an exposed tissue contacting surface 204, as well as an inner surface (not shown here) that abuts the spacer top surface 250. A portion of spacer top surface 250 also forms part of the tissue contacting surface. Screen electrode 202 abuts spacer top surface 250 with minimal gaps, deterring fluid ingress and energy misdirection. In some embodiments, such as that shown in FIG. 3a, active electrode 202 defines an exposed lateral edge surface 205, free of any asperities or internal pointed geometry 214a, b to allow a side ablative effect for application on certain more sensitive tissue types such as cartilage. Use of the lateral edge surface 205 also allows for maximum visibility of the electrode surface 204 and the associated tissue effect. As shown in FIG. 3c, a cross section A-A of FIG. 3b, active electrode aperture 206 is fluidly coupled to the flexible tubular member 116 (shown in FIG. 3c) via a spacer aspiration cavity 256.

As illustrated best in FIGS. 3b, 3c and FIG. 4, spacer cavity 256 defines an elongate shaped opening at spacer top surface 250. Spacer cavity 256 fluidly communicates with electrode aperture 206 and extends in a proximal and distal direction beyond the proximal edge surface 212 and distal edge surface 210 of active electrode 202, so as to define a distal aperture 252 and proximal aperture 254. Spacer cavity 256 tapers from an elongate opening at the top surface 250 to an approximate circular cross section 255 within spacer 200 which gives cavity 256 an elongated funnel-like shape. Cavity taper may have an angle in the range of about 140-170°, and preferably about a 157° angle relative to the contact surface 204 as shown in FIG. 3c. This angle defines a maximum gap X between the active electrode inner surface 218 and beginning of circular cross section 255 of aspiration conduit, so as to minimize clogging of the aspiration tubing and conduits due to larger debris sizes. Gap X may be in the range of about 0.1 to 1 mm, preferably about 0.3-0.6 mm. Debris or tissue fragments larger than gap X in dimension will become trapped within gap X and continue to be fragmented by the ablative effect proximate active electrode inner surface 218 until the debris or tissue fragment is reduced in size, free to be aspirated through cross section 255 while being less likely to clog any downstream aspiration conduits or lumens, such as lumen 116.

Spacer cavity 256, via apertures 252, 254 and in cooperation with the screen electrode distal and proximal edge surfaces 210 and 212 respectively, define a multitude of aspiration apertures adjacent to or at the electrode contact surface 204, all of which are fluidly connected within cavity 256 of spacer 200. Distal aperture 252 has a continuous perimeter defined partially by the electrode distal edge surface 210 and partially by the distal portion of the spacer cavity 256. As shown in FIG. 3b, the perimeter also includes at least one internal cusp 214a. Proximal aperture 254 has a perimeter defined partially by the electrode proximal edge surface 212, including at least one cusp 214b and partially by a proximal portion of the cavity 256. Proximal aperture 254 extends a first distance "E" beyond active electrode proximal edge 212, while distal aperture 252 extends a second distance "e" beyond active electrode distal edge 210. In order to have a more balanced flow between the distal aperture 252 and proximal aperture 254, it has been found that extension "E" should be larger than extension "e". This is due to differing aspiration rates between the two apertures (252 and 254) predominantly as a result of the difference in transitions angles, 260 and 262. Looking at FIG. 3c, it can be seen that transition angle 260 defines a shallower angle relative to transition angle 262, and results in a preferential aspiration of debris through the distal aperture 252. Increased aspiration may lead to preferential electrode erosion adjacent the area of increased aspiration, so proximal aperture 254 is therefore relatively larger than distal aperture 252 in order to better balance aspiration flow across the tissue contact surface 204 and to mitigate potential erosion to any particular portion of the active electrode 202 around each aperture.

Spacer apertures 252 and 254 and electrode aperture 206 provide conduits for fluid and gas bubbles to be aspirated away from the area surrounding active electrode 202. During arthroscopic surgical procedures the visual field near the surgical site (i.e., near the active electrode) may be obscured by gas bubbles. That is, the process of ablation via tissue contact with the vapor layer described above creates gas bubbles, and in many situations the gas bubbles are quickly aspirated away so as not adversely affect the visual field. However, excessive aspiration too close to a portion of the active electrode 202 that is treating the target tissue may interrupt the vapor layer and hence the uniformity of ablative tissue effect. Apertures 206, 252 and 254 are therefore spaced away, in discrete locations, from the lateral side edge surface 205. Apertures 206, 252 and 254 are disposed between the lateral side edge surface 205 and the primary surgical field viewing portal so as to effectively remove bubbles created predominantly at lateral edge surface 205 which then naturally elevate towards apertures 206, 252 and 254. This is thought to improve surgeon visibility of the surgical field while minimally impacting the vapor layer near the lateral edge surface 205.

A detailed perspective view of spacer is shown in FIG. 4, in accordance with some embodiments, to better describe spacer cavity 256 and securement wire conduits 258. Spacer cavity 256 may be shaped in an elongate funnel form or plenum within spacer that tapers to a more circular cross section 255 (see in FIG. 3c) at a more proximal location of spacer 200, so as to interface with a fluid tube 116 (shown in FIG. 3c) disposed within elongate shaft. Securement wire conduits 258 may be uniform in cross section and extend axially through the entire thickness of spacer 200 to allow passage for securement wires 220 through spacer 200. Spacer 200, being made from an electrical insulating material, may electrically isolate securement wires 220 (shown in FIG. 3b) from each other as well as from return electrode 203. In alternative embodiments, securement wires 220 may have an electrically insulative coating. Securement wires 220 extend proximally through shaft 106 and may electrically couple with multi-conductor cable 112 within handle 110 (not shown here).

FIG. 5 representatively illustrates in greater detail a typical treatment of a target tissue 300 by use of an embodiment of electrosurgical wand 102 according to the present disclosure. Initially, surgeon may place a spacer lateral side 240 on the tissue and roll wand distal end portion 108 toward spacer lateral edge bevel 241 while applying energy, until a tissue effect is observed. This will occur once electrode lateral edge surface 205 is sufficiently close to target tissue 300, or in contact. As shown, the high frequency voltage is sufficient to convert the electrically conductive fluid 310 between the target tissue 300 and active electrode 202 into a vapor layer 312 or plasma.

During the process, gases 320 and debris will be aspirated through apertures 206, 252 or 254 to a vacuum source (not shown). In addition, excess electrically conductive fluid, and other fluids (e.g., blood) will be aspirated from the target site 300 to facilitate the surgeon's view. Gas bubbles 320 may naturally rise from the vapor or plasma layer 312, upwards or in a medial direction towards apertures 206, 252 or 254 and be removed so as to improve surgeon's target tissue visualization.

Figure 6:
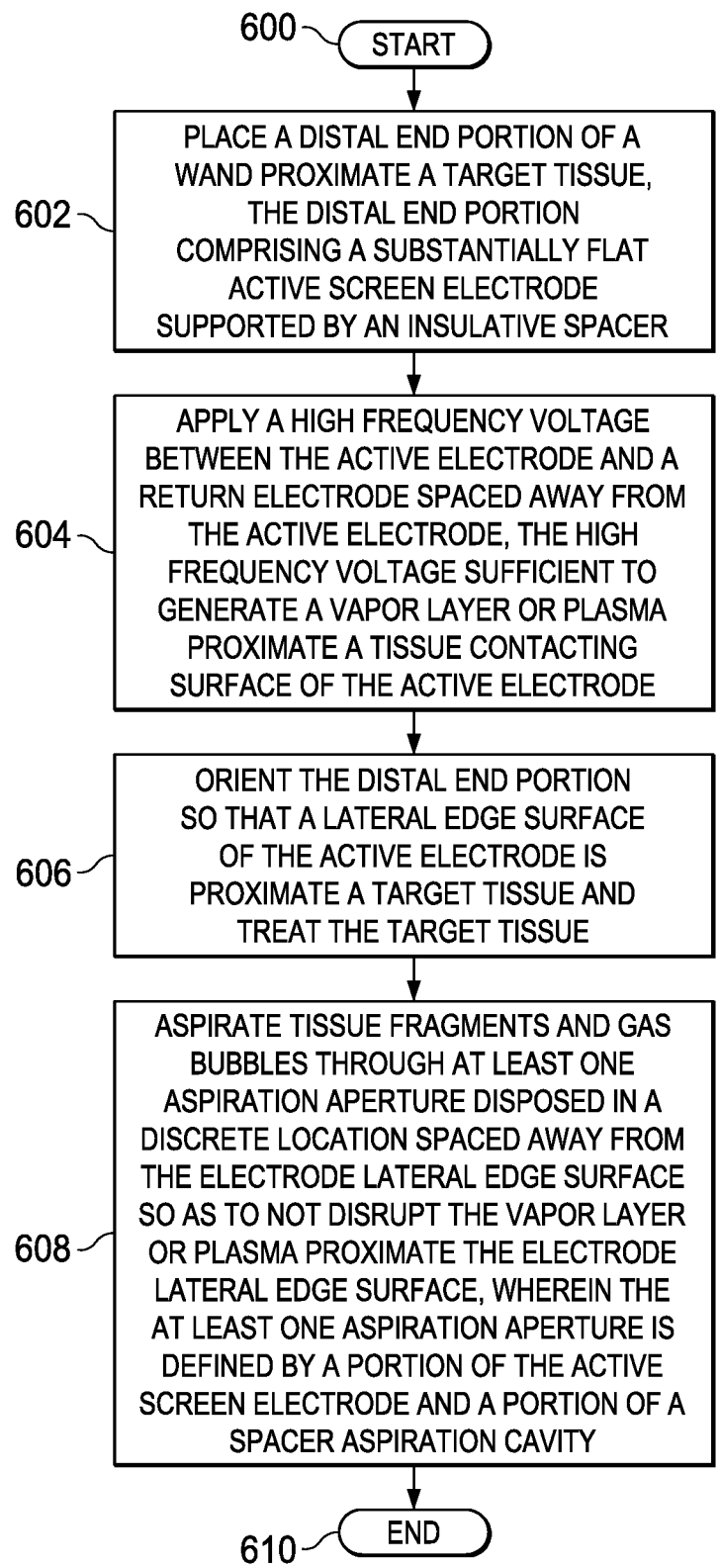
FIG. 6 shows a method of treating tissue in accordance with at least some embodiments.

FIG. 6 shows a method in accordance with at least some embodiments. In particular, the method starts (block 600) and proceeds to: placing a distal end portion of the wand proximate a target tissue, the distal end portion comprising a substantially flat active screen electrode and an insulative spacer, the screen electrode supported by the spacer (block 602); applying a high frequency voltage between the active electrode and a return electrode spaced away from the active electrode, the high frequency voltage sufficient to generate a vapor layer or plasma proximate a tissue contacting surface of the active electrode (block 604); orienting the distal end portion so that a lateral edge surface of the active electrode is proximate a target tissue and treating the target tissue (block 606); and aspirating tissue fragments and gas bubbles through at least one aspiration aperture disposed in a discrete area spaced away from the lateral edge surface so as to not disrupt the vapor layer or plasma proximate the active electrode lateral edge surface, wherein the at least one aspiration aperture is defined by a portion of the active screen electrode and a portion of a spacer aspiration cavity (block 608). The method may also include at least three aspiration apertures and wherein the step of aspirating further comprises aspirating the tissue fragments and gas bubbles approximately equally through the at least three aspiration apertures, wherein the at least three apertures are coplanar on a plane spaced away from the lateral edge surface and the at least three apertures are approximately evenly spaced and of differing sizes so as to uniformly aspirate along a length of the lateral edge surface. The method may also include generating a vapor layer or plasma proximate a geometric feature capable of creating a point of high current density on the active electrode, wherein the geometric feature may comprise an internal cusp. Thereafter, the method ends (block 610).

Figure 7:
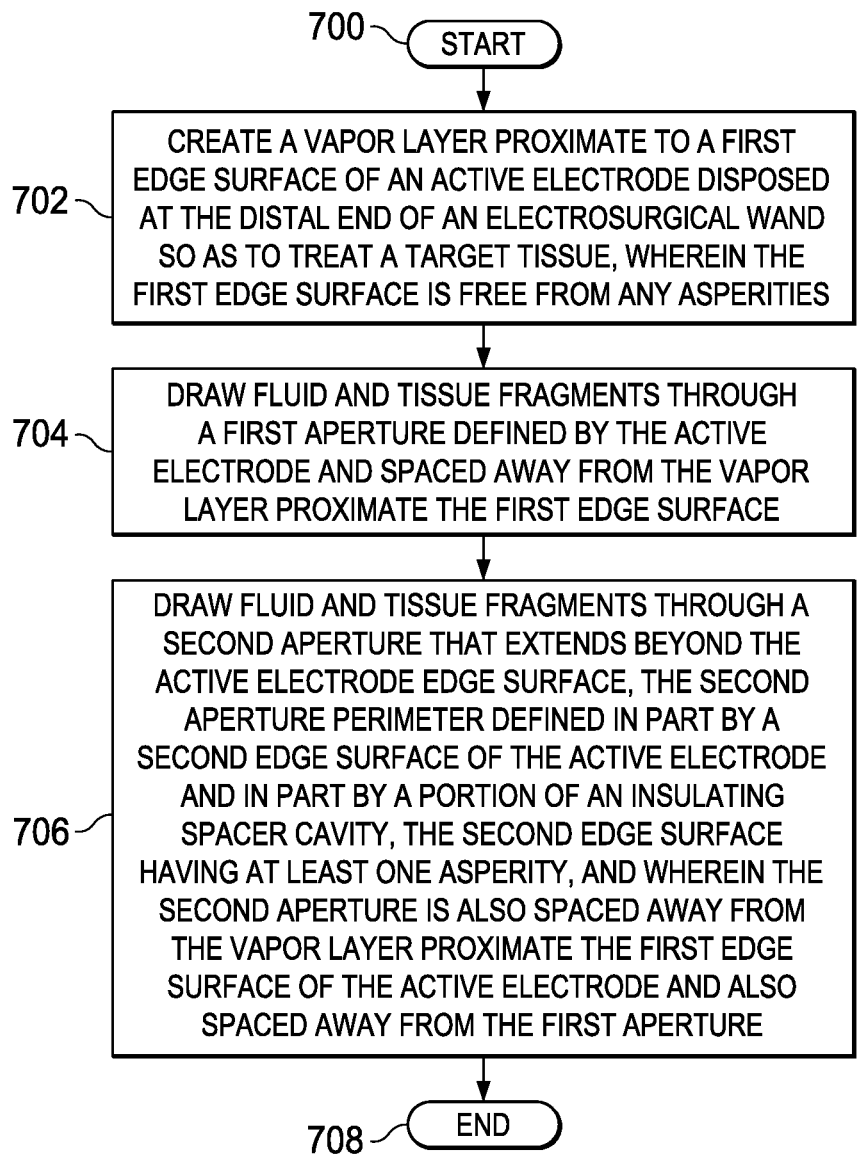
FIG. 7 shows a method of treating tissue in accordance with at least some embodiments.

FIG. 7 shows a method in accordance with at least some embodiments. In particular, the method starts (block 700) and proceeds to: creating a vapor layer proximate to a first edge surface of an active electrode disposed at the distal end of an electrosurgical wand so as to treat a target tissue, wherein the first edge surface is free from any points of high current density (block 702); drawing fluid and tissue fragments through a first aperture defined by the active electrode only and spaced away from the vapor layer proximate the first edge surface (block 704), drawing fluid and tissue fragments through a second aperture that extends beyond an active electrode edge surface, the second aperture perimeter defined in part by a second edge surface of the active electrode and in part by a portion of an insulating spacer cavity, the second edge surface having at least one internal or external pointed geometry or surface asperity, and wherein the second aperture is also spaced away from the vapor layer proximate the first edge surface of the active electrode and also spaced away from the first aperture (block 706). The method may further comprise drawing fluid and tissue fragments through a third aperture, the third aperture defined in part by a third edge surface of the active electrode and in part by a portion of the insulating spacer cavity and wherein the first, second and third aperture are all fluid coupled. Thereafter, the method ends (block 708).

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter, and because many modifications may be made in the embodiments herein detailed in accordance with the descriptive requirements of the law, it is to be understood that the details herein are to be interpreted as illustrative and not in a limiting sense.

What is claimed is:

1. A method of treating a target tissue using an electrosurgical wand comprising:
   placing a distal end portion of the wand proximate the target tissue, the distal end portion comprising an active electrode and an insulative spacer, the active electrode supported by the spacer;
   applying a high frequency voltage between the active electrode and a return electrode spaced away from the active electrode, the high frequency voltage sufficient to generate a vapor layer proximate a tissue contacting surface of the active electrode;
   orienting the distal end portion so that a lateral edge surface of the active electrode is proximate the target tissue and treating the target tissue; and
   aspirating gas bubbles through at least one aspiration aperture disposed in a discrete location spaced away from the active electrode lateral edge surface, configured so as to minimally disrupt the vapor layer proximate the active electrode lateral edge surface, wherein the at least one aspiration aperture has a perimeter defined by a portion of the active electrode and a portion of a spacer aspiration cavity.

2. The method of claim 1 wherein the at least one aspiration aperture perimeter is defined by an outer peripheral edge of the active electrode and a portion of a perimeter of the spacer cavity.

3. The method of claim 1 wherein the at least one aspiration aperture comprises a plurality of aspiration apertures, each spaced from the active electrode lateral edge surface so that aspirating the gas bubbles further comprises aspirating the gas bubbles approximately equally through the plurality of aspiration apertures.

4. The method of claim 3 wherein the plurality of aspiration apertures are configured so as to uniformly aspirate along a length of the active electrode lateral edge surface.

5. The method of claim 1 wherein the active electrode lateral edge surface is free of any asperities.

6. The method of claim 1 wherein the step of aspirating further comprises aspirating tissue fragments and gas bubbles through at least one electrode aperture disposed in the discrete location spaced away from the active electrode lateral edge surface and the at least one aspiration aperture so as to not disrupt the vapor layer proximate the active electrode lateral edge surface, the electrode aperture having a periphery defined entirely by the active electrode.

7. The method of claim 1 wherein the at least one aspiration aperture comprises two aspiration apertures configured so that aspirating the gad bubbles further comprises aspirating from opposing ends of the active electrode.

8. The method of claim 1 wherein the portion of the active electrode defines at least one asperity, and wherein aspirating the gas bubbles further comprises drawing tissue fragments away from the active electrode lateral edge surface and through the at least one aspiration aperture and fragmenting the tissue fragments adjacent to the at least one asperity.

9. The method of claim 1 wherein aspirating the gas bubbles defines a flow path starting at the lateral edge surface of the active electrode moving over the tissue contacting surface of the active electrode and towards and over an outer peripheral edge surface of the active electrode and into the at least one aspiration aperture.

10. The method of claim 1 wherein the active electrode is supported on a distal end surface of the spacer, the distal end surface defining an outer periphery, and therein the active electrode lateral edge surface is coincident with a portion of the spacer outer periphery.

11. A method of treating a target tissue using an electrosurgical wand comprising:
   placing a distal end portion of the wand near the target tissue, the distal end portion comprising an active electrode disposed on an insulative spacer;
   supplying a high frequency voltage to the active electrode, the high frequency voltage configured to generate a vapor layer near a tissue contacting surface of the active electrode;
   orienting the distal end portion so that an active electrode lateral edge surface is adjacent the target tissue;
   aspirating tissue fragments and gas bubbles away from the active electrode lateral edge surface, over the tissue contacting surface, over an outer peripheral edge surface of the active electrode and through at least one aspiration aperture, the at least one aspiration aperture abutting the outer peripheral edge surface of the active electrode.

12. The method of claim 11 wherein the at least one aspiration aperture has a perimeter that is at least partially defined by the outer peripheral edge surface of the active electrode and a perimeter of a spacer aspiration cavity.

13. The method of claim 11 wherein the at least one aspiration aperture comprises a plurality of aspiration apertures, each spaced from the active electrode lateral edge surface so as to aspirate the tissue fragments and gas bubbles approximately equally through the plurality of aspiration apertures.

14. The method of claim 11 wherein the active electrode lateral edge surface is coincident with a lateral edge surface of the insulative spacer.

15. The method of claim 11 wherein the at least one aspiration aperture is defined by a portion of the active electrode that has at least one asperity, configured so as to further fragment tissue fragments as they are aspirated through the at least one aspiration aperture.

16. A method of treating a target tissue using an electrosurgical wand comprising:
 orienting the wand so as to place a first edge surface of an active electrode adjacent the target tissue;
 supplying a high frequency voltage between the active electrode and a return electrode, the high frequency voltage configured to generate a vapor layer along the first edge surface;
 generating gas bubbles along the first edge surface; and
 drawing the gas bubbles away from the first edge surface, over an outer peripheral edge surface of the active electrode spaced away from the first edge surface and through at least one aspiration aperture.

17. The method of claim 16 further comprising treating tissue so as to generate tissue fragments and drawing the tissue fragments over the outer peripheral edge surface of the active electrode, through the at least one aspiration aperture.

18. The method of claim 16 wherein the outer peripheral edge surface further comprising at least one asperity so as to further fragment some of the tissue fragments while drawing the tissue fragments over the outer peripheral edge surface of the active electrode.

19. The method of claim 16 wherein the at least one aspiration aperture has a perimeter that is defined by the peripheral edge surface of the active electrode and a perimeter of a spacer cavity.

* * * * *